US009474674B2

(12) United States Patent
Bue, Jr. et al.

(10) Patent No.: US 9,474,674 B2
(45) Date of Patent: Oct. 25, 2016

(54) PROPRIOCEPTIVE TOPICAL LEG GEAR AND METHODS OF USE

(71) Applicant: TOPICAL GEAR, LLC, Austin, TX (US)

(72) Inventors: William D. Bue, Jr., Austin, TX (US); Elizabeth Danflous Russell, Austin, TX (US)

(73) Assignee: Topical Gear, LLC, Lakeway, TX (US)

( * ) Notice: Subject to any disclaimer, the term of this patent is extended or adjusted under 35 U.S.C. 154(b) by 672 days.

(21) Appl. No.: 14/035,725

(22) Filed: Sep. 24, 2013

(65) Prior Publication Data

US 2014/0088475 A1    Mar. 27, 2014

Related U.S. Application Data

(60) Provisional application No. 61/705,134, filed on Sep. 24, 2012.

(51) Int. Cl.
| | |
|---|---|
| *A61F 13/00* | (2006.01) |
| *A61H 1/00* | (2006.01) |
| *A61F 13/08* | (2006.01) |
| *A61H 39/04* | (2006.01) |
| *A63B 71/12* | (2006.01) |

(52) U.S. Cl.
CPC ............... *A61H 1/006* (2013.01); *A61F 13/08* (2013.01); *A61H 39/04* (2013.01); *A61H 2201/164* (2013.01); *A61H 2201/165* (2013.01); *A63B 2071/1258* (2013.01); *A63B 2209/10* (2013.01)

(58) Field of Classification Search
CPC ..... A41D 13/05; A61F 13/08; A61F 5/0111; A61H 1/006; A61H 2201/164; A61H 2201/165; A61H 39/04; A63B 2071/1258; A63B 2209/10; A43B 5/10; A43B 7/20; A61B 17/809; A61B 2017/922; A61B 17/0642; A61B 17/1728; A61B 17/8061; A61B 17/70; A61B 17/7056; A61B 17/86; A61B 17/1739; A61B 17/808; A61B 17/92; A61B 2017/1775; A61B 17/0401
USPC .......................... 602/23–28, 60–65; 128/882
See application file for complete search history.

(56) References Cited

U.S. PATENT DOCUMENTS

| | | | | |
|---|---|---|---|---|
| 958,199 | A * | 5/1910 | Ward ..................... | A61F 13/063 128/894 |
| 4,323,058 | A * | 4/1982 | Detty ..................... | A61F 5/0111 602/27 |
| 5,810,754 | A * | 9/1998 | Kenosh ................. | A61F 5/0111 602/27 |
| 6,692,454 | B1 * | 2/2004 | Townsend ............... | A43B 5/10 128/882 |

\* cited by examiner

*Primary Examiner* — Michael Brown
(74) *Attorney, Agent, or Firm* — Rodney J. Fuller; Booth Udall Fuller, PLC

(57) ABSTRACT

A topical leg gear for enhancing performance and reducing the risk of injury. The topical leg gear and kits preferably comprise a flexible sleeve and a lateral foot-ankle buttress, malleolus bone buttresses, and a peroneal longus buttress. The topical leg gear is designed to be worn during periods of physical activity to reduce injury and to train and strengthen the athletes' muscles against injury, advantageously increasing proprioception, neuromuscular communication or both by stimulating critical sensory and tactile receptors in the leg, foot, and ankle. Performance can be enhanced and risk of injury reduced by use of the topical leg gear through isolating, activating, and training muscles to stimulate a stretch reflex, reduce latency in muscle spindles, and speed up a reaction time of muscles by reducing delay in muscle reaction times.

20 Claims, 6 Drawing Sheets

US 9,474,674 B2

PROPRIOCEPTIVE TOPICAL LEG GEAR AND METHODS OF USE

CROSS REFERENCE TO RELATED APPLICATIONS

This document claims the benefit of U.S. Provisional Application No. 61/705,134, entitled "Proprioceptive Topical Leg Gear and Methods of Use", which was filed on Sep. 24, 2012, the disclosure of which is incorporated by reference in its entirety.

FIELD OF THE INVENTION

This invention relates to topical leg gear for enhancing performance and reducing the risk of injury. The topical leg gear preferably comprises a flexible sleeve with at least one buttress. It is designed to be worn during periods of physical activity. The invention increases proprioception, neuromuscular communication or both by stimulating critical sensory and tactile receptors in the leg, foot, and ankle. Performance can be enhanced and risk of injury reduced by the topical leg gear through isolating, activating, and training muscles to stimulate a stretch reflex, reduce latency in muscle spindles, and speed up a reaction time of muscles by reducing delay in muscle reaction times.

BACKGROUND OF THE INVENTION

Ankle braces have long been a fixture in the realm of sports medicine and athletic training. For decades, the ankle brace market has relied on bulky, rigid designs and taping. Indeed, current ankle braces trace their origins to stirrup-based designs patented in the 1890's. See, e.g. U.S. Pat. No. D29,415 (filed Aug. 31, 1898). Other designs resemble a standard tape job frequently applied to an athlete by an athletic trainer. Such braces rely on outmoded technology and fail to address the latest in neuromuscular research. Moreover, although some of these braces purportedly prevent injury, most are designed for application post-injury, as a means of treating foot and ankle injuries after the fact. A growing number of experts (including those with the most practical experience with ankle braces, such as athletic trainers and coaches) are recognizing the shortcomings of the current crop of ankle braces: typically making the ankle weaker, transferring load up the limb, and restricting range of motion of the ankle and foot. The prior art ankle braces were not designed to strengthen and condition the ankle naturally. As a result, a need exists for topical leg gear that will proactively strengthen the ankle and reduce the risk of injury.

BRIEF SUMMARY OF THE INVENTION

The present invention provides topical leg gear which proactively strengthens the ankle and reduces the risk of injury. Instead of a rigid, restrictive brace, the present invention combines a flexible sleeve with a lateral foot-ankle buttress, two malleolus bone buttresses and a peroneal longus buttress. This invention applies topical pressure to select areas of the leg, foot and ankle, thereby stimulating critical neuroreceptors and improving the user's proprioception, neuromuscular communication, motor skills, Hoffman reflex ("H-reflex"), and overall flexibility.

In one embodiment, the invention is directed to topical leg gear for enhancing performance and/or reducing the chance of injury. The leg gear preferably comprises a combination of one or more of the following elements: a flexible sleeve having an interior and an exterior surface; and at least one buttress coupled to the interior of the flexible sleeve such that when the leg gear is worn by a user, the at least one buttress applies sufficient pressure to at least a portion of at least one of a muscle, tendon, bone or ligament of the lower leg to increase proprioception, neuromuscular communication or both in the user.

In a preferred embodiment, the topical leg gear comprises four buttresses. For example, a peroneal longus buttress placed on the belly of the peroneal longus muscle and configured to apply sufficient pressure to the user's muscle portion of the peroneal longus such that the chance of injury is reduced; a first malleolus bone buttress configured to apply sufficient pressure to the user's medial malleolus such that the chance of injury is reduced; a second malleolus bone buttress configured to apply sufficient pressure to the user's lateral malleolus such that the chance of injury is reduced; and a lateral foot-ankle buttress configured to apply sufficient pressure to the user's lateral ligaments of the ankle such that the chance of injury is reduced. The at least four buttresses are configured to increase proprioception, neuromuscular communication or both to correct a user's talus to its normal anatomical relationship within a user's fibula-tibia joint.

The peroneal longus buttress is preferably no more than about 5.08 centimeters (cm) or 2 inches long and no more than about 2.54 cm or 1 inch wide. In addition, preferably the peroneal longus buttress and the first and second malleolus bone buttresses are no more than 0.85 cm or ⅓ inches thick and are substantially elliptical.

In a specific embodiment, the topical leg gear comprises lateral foot-ankle buttress having a flared upper portion having a first region that is configured to extend over and provide resistance to an anterior portion of the foot and a second region that is configured to fit in close proximity to, but under a user's lateral malleolus; and a medial portion configured to conform to and extend around a user's foot, while providing resistance to a lateral portion of the foot. An example of a preferred flexible sleeve is one that comprises a material that provides 4-way compression.

The invention is also directed to a method of enhancing an athlete's performance and/or reducing the chance of injury of a user. The preferred method comprises applying the leg gear as described herein to the user's leg during physical activities over an interval of time. For example, the leg gear is applied during one or more activity selected from the group consisting of: resistance training, agility training, endurance training, rehabilitation and competitive activities.

Furthermore, the invention is directed to a system of topical pressure buttress placements to enhance performance and/or reduce the chance of injury. In a preferred embodiment the system comprises: a primary buttress placement located on a portion of skin over the belly of a user's peroneal longus muscle; a secondary buttress placement located on a portion of skin on the back side of a user's medial malleolus and lateral malleolus; a tertiary buttress placement located on a portion of skin over a user's lateral ligaments of the ankle.

In yet another embodiment, the invention is directed to a proprioceptive topical leg gear kit useful for enhancing a user's performance and/or reducing the chance of injury. The kit typically comprises: a flexible sleeve having an interior and an exterior surface; and at least one buttress configured to couple to the flexible sleeve and conform to at least a portion of at least one of a muscle, tendon, bone or ligament of the lower leg to increase proprioception, neuromuscular communication or both in a user.

BRIEF DESCRIPTION OF THE DRAWINGS

Illustrative and exemplary embodiments of the invention are shown in the drawings in which.

Figure 1:
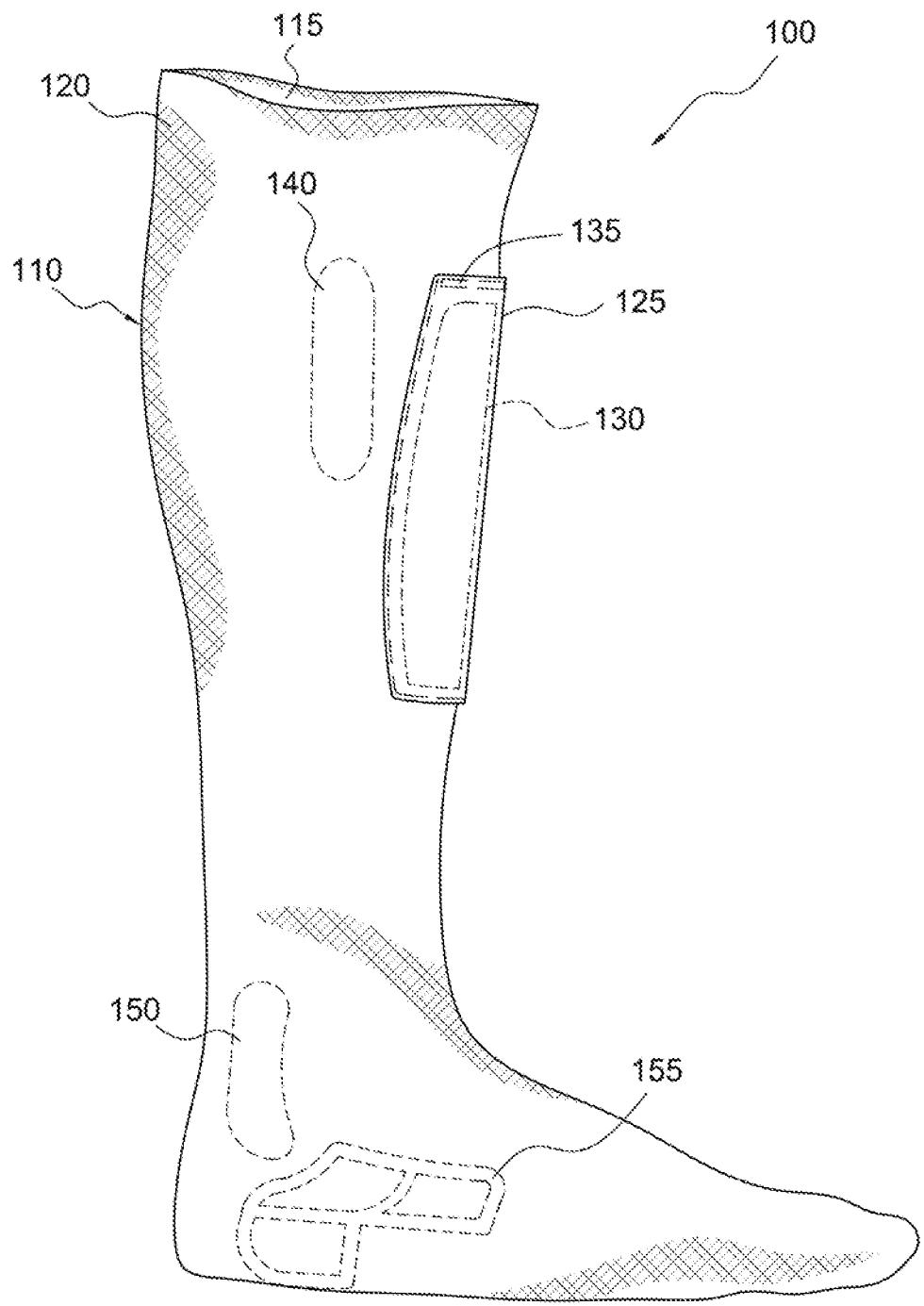
FIG. 1 is a side view of topical leg gear using thickening weave buttresses.

Elements and facts in the figures are illustrated for simplicity and have not necessarily been rendered according to any particular sequence or embodiment.

DETAILED DESCRIPTION OF THE INVENTION

Aspects and applications of the invention presented here are described below in the drawings and detailed description of the invention. Unless specifically noted, it is intended that the words and phrases in the specification and the claims be given their plain, ordinary and accustomed meaning to those of ordinary skill in the applicable arts.

The following is a description of the preferred embodiments of the present invention and is not intended to limit the scope of the invention to the particular embodiments discussed below.

FIG. 1 illustrates a preferred embodiment of topical leg gear 100 for enhancing performance and reducing the risk of injury. Topical leg gear 100 comprises a flexible sleeve 110 and at least one buttress which applies topical pressure to part of a user's lower leg, typically to the peroneal muscle group.

In a preferred embodiment, the flexible sleeve 110 has an interior surface 115 and an exterior surface 120 and is comprised of a thin, resilient, radially stretchable material that provides compression to the at least one buttress. In a more preferred embodiment, the flexible sleeve 110 provides 4-way compression to the at least one buttress. In a particular embodiment, the flexible sleeve 110 is a flexible compression sleeve, or compression sock, to more effectively provide pressure on the user's leg, foot and ankle to increase proprioception, neuromuscular communication or both. A loose-knit fiber may be used as the material for the flexible sleeve 110 and the loose-knit fiber can be any one of a number of commercially available stretchable materials such as LYCRA, SPANDEX, BIOSKIN, or EpX. Various combinations of nylon, elasthan, polyester, polymid, and laytex are also encompassed and included in preferred materials. Most preferably, the flexible sleeve is comprised of a material comprising 85% Polyamid and 15% Elasthan. However, the flexible sleeve 110 is not limited to these materials.

Figure 2:
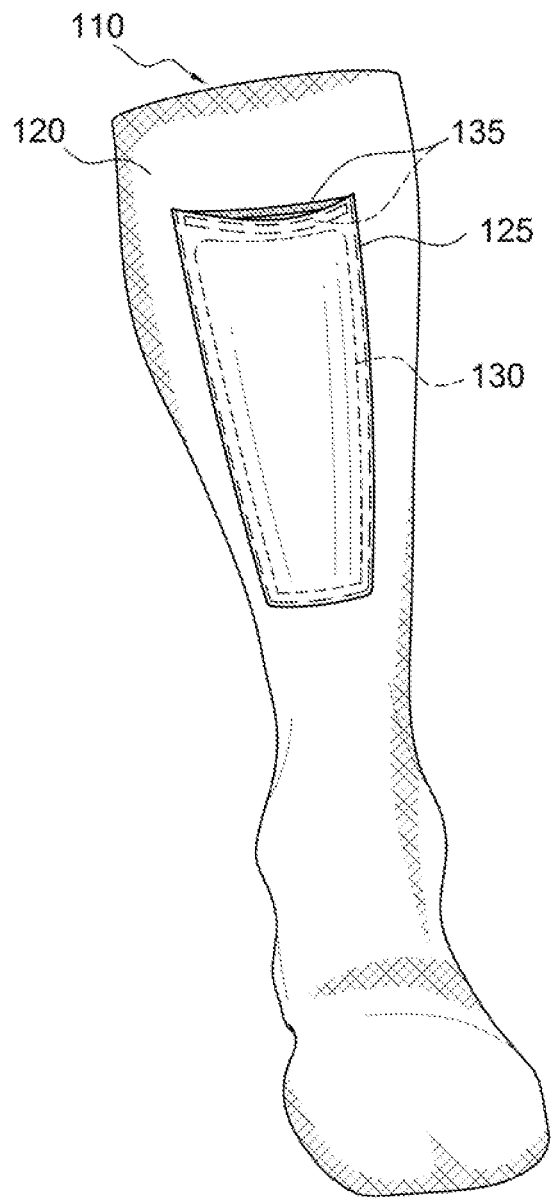
FIG. 2 is a front view of the topical leg gear of FIG. 1.
Figure 3:
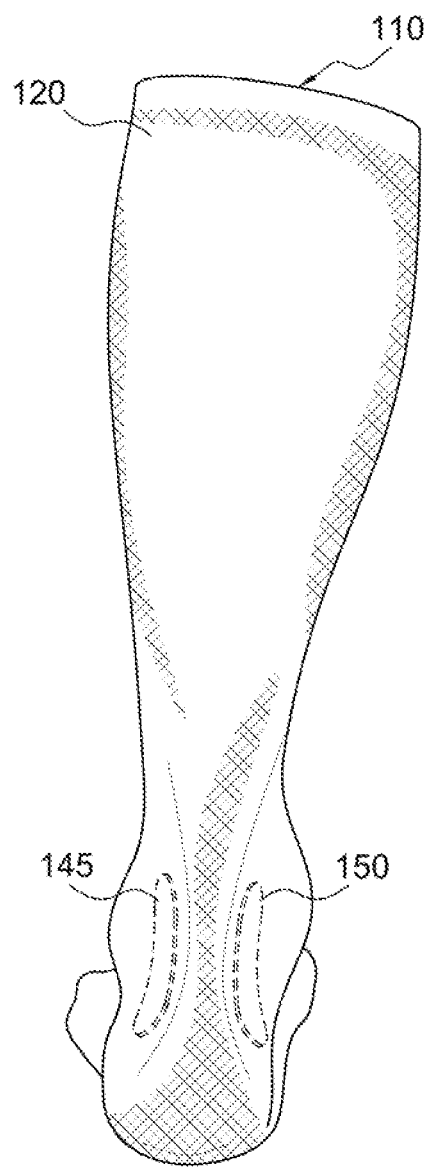
FIG. 3 is a back view of the topical leg gear of FIG. 1.
Figure 4:
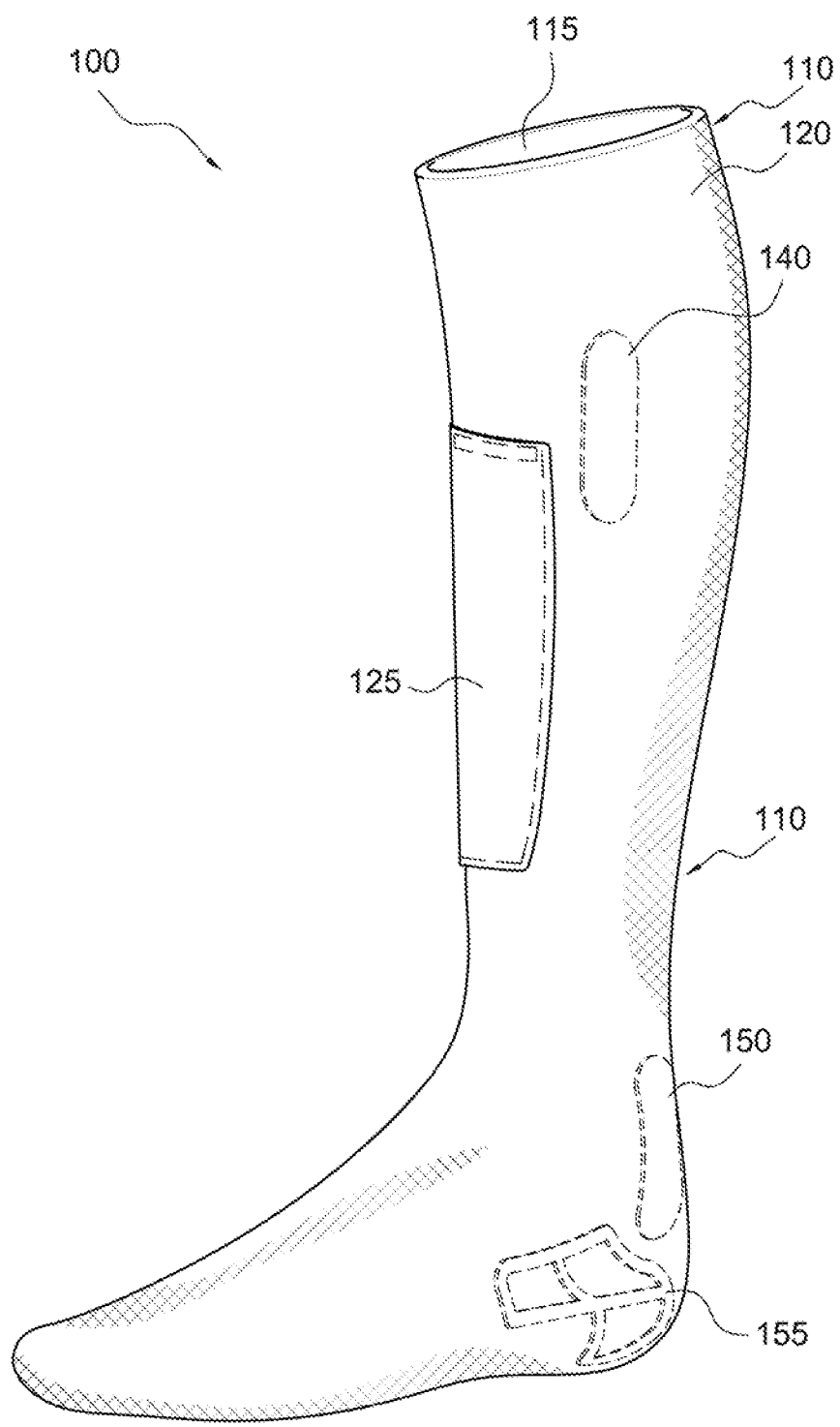
FIG. 4 is a perspective view of the topical leg gear of FIG. 1.

Preferably, the flexible sleeve 110 is a sock 110, and most preferably, the flexible sleeve 110 is a knee-high sock 110, as illustrated in FIG. 1, which extends past a user's calf and reaches or almost reaches the user's knee when worn. In a preferred embodiment, a pocket 125 is coupled to the flexible sleeve 110. As shown in FIG. 2, the pocket 125 is sized and shaped to hold a shin guard 130 and is typically coupled to the exterior surface 120 of the flexible sleeve 110; however, in particular embodiments, the pocket 125 may be coupled to the interior surface 115 of the flexible sleeve 110. The pocket 125 is positioned on the flexible sleeve 110 so the shin guard 130 placed inside the pocket 125 will protect the shinbone of a user while involved in an athletic event, specifically a soccer game or practice. In one aspect, the pocket 125 is configured to receive the shin guard 130 through a top portion closest to the user's knee, and the sides and bottom portions are sealed. In alternative embodiments, portions other than the top portion may receive the shin guard 130 into the pocket 125.

In a particular embodiment, one aspect of the pocket 125 further comprises a fastening device 135 to close the pocket 125 to fully enclose the shin guard 130 and prevent it from falling out while topical leg gear 100 is in use. Preferably, laces are used as the fastening device 135. More preferably, a zipper is used as the fastening device 135. Most preferably, Velcro or hook loop fasteners are used as the fastening device 135. Any other fastening device may also be used to secure the shin guard 130 in the pocket 125. In alternative embodiments, the pocket 125 is sized so that its length does not allow the shin guard 130 to be fully enclosed within the pocket 125. For example, the length of the pocket 125 may be approximately half of the length of the shin guard 130. Other lengths of the pocket 125 are also contemplated that will secure the shin guard during use. In a preferred embodiment, the pocket 125 is sewn to the flexible sleeve 110 on three sides as discussed above. In an alternative embodiment not shown, topical leg gear 100 further comprises a shin guard 130 incorporated into the flexible sleeve 110, positioned between the interior surface 115 and the exterior surface 120. This particular embodiment does not require a pocket 125 to hold the shin guard 130.

Figure 5:
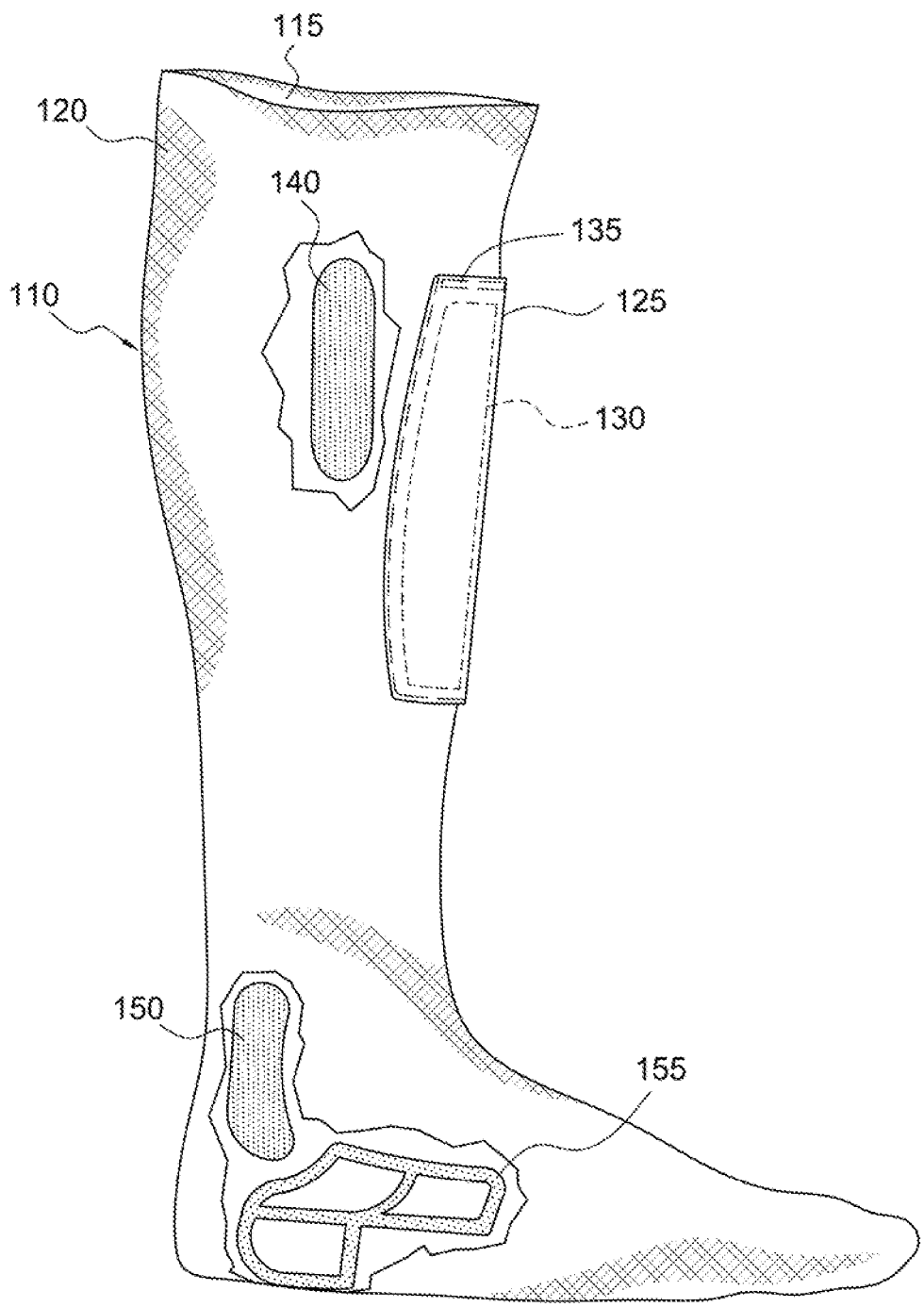
FIG. 5 is a side view of topical leg gear using foam buttresses.

The at least one buttress is preferably coupled to the interior surface 115 of the flexible sleeve 110. When topical leg gear 100 is worn by a user, the at least one buttress, under compression from the flexible sleeve 110, applies topical pressure to at least one of a muscle, tendon, bone or ligament of the lower leg, which increases proprioception, neuromuscular communication in the user, or both. Preferably, the at least one buttress comprises any compressible material that is light and thin. More preferably, the at least one buttress comprises air, gel or gel-like material. Most preferably, the at least one buttress comprises a compressible foam or foam-like material (see FIG. 5). In a preferred embodiment, the at least one buttress is coupled to the flexible sleeve 110 with Velcro or hook loop fasteners. In a more preferred embodiment, the at least one buttress is sewn into the flexible sleeve 110, as in FIG. 5. In a most preferred embodiment, the at least one buttress is formed by a thickening weave in the flexible sleeve, as in FIG. 1.

Figure 6:
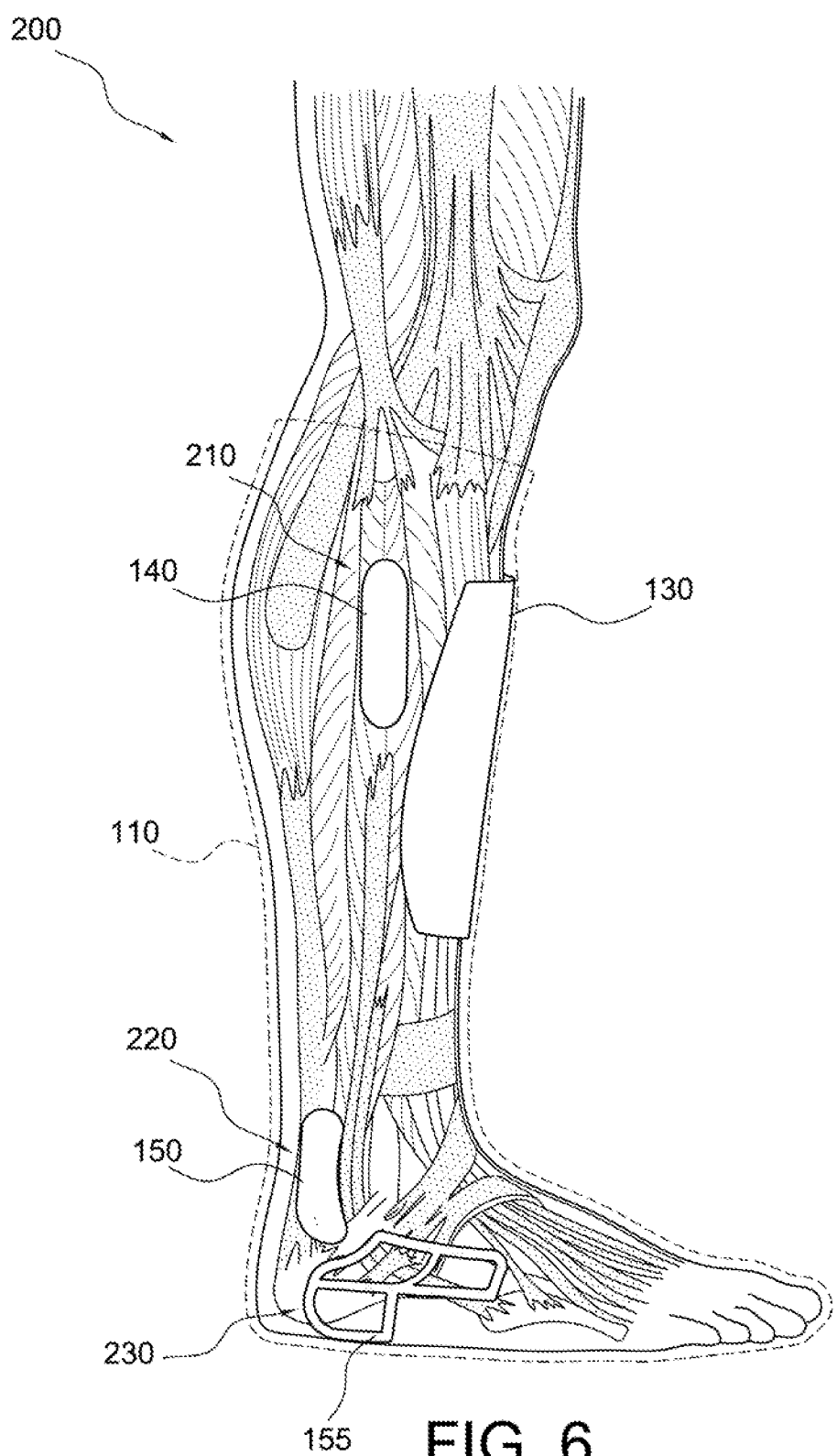
FIG. 6 is a side view of a human leg showing a buttress placement system for increasing proprioception, neuromuscular communication or both.

FIGS. 1-4 illustrate a preferred embodiment in which topical leg gear 100 comprises four buttresses 140, 145, 150 and 155: a peroneal longus buttress 140, a first malleolus bone buttress 145, a second malleolus bone buttress 150, and a lateral foot-ankle buttress 155. In a most preferred embodiment, the four buttresses 140, 145, 150 and 155 are positioned according to a system of topical pressure buttress placements 200, as shown in FIG. 6. Preferably, the system of topical pressure buttress placements 200 comprises a primary buttress placement 210, a secondary buttress placement 220 and a tertiary buttress placement 230. The primary buttress placement 210 is located on a portion of skin over a muscle portion of a user's peroneal longus. In a most preferred embodiment, the primary buttress placement 210 is placed on the muscle belly of a user's peroneal longus. The secondary buttress placement 220 is located on a portion of skin on the back side of a user's medial malleolus and lateral malleolus. The tertiary buttress placement 230 is located on a portion of skin over a user's lateral ligaments of the ankle.

In a preferred embodiment, the peroneal longus buttress 140 is positioned at the primary buttress placement 210 on the muscle belly of the peroneal longus, the first and second malleolus bone buttresses 145 and 150 are positioned on the medial and lateral side of the secondary buttress placement 220, respectively, and the lateral foot-ankle buttress 155 is positioned at the tertiary buttress placement 230. In this configuration, the four buttresses 140, 145, 150 and 155 work as a system to increase proprioception, stimulate neuromuscular communication or both in order to correct a user's talus to its normal anatomical relationship within the user's fibula-tibia joint.

The peroneal longus buttress 140 is configured such that when topical leg gear 100 is worn by a user, the peroneal longus buttress 140 applies sufficient pressure to the user's muscle portion of the peroneal longus to increase neuromuscular communication and reduce the risk of injury. More specifically, the peroneal longus buttress 140 is placed so that it applies sufficient pressure to the muscle belly of the peroneal longus to provide the desired results. Although the peroneal longus buttress primarily increases neuromuscular communication, it may also function to increase proprioception. For example, when a user's ankle joint experiences stress, the proprioception mechanism initiates a muscle contraction of the peroneal longus. The superficial peroneal nerve, which innervates the peroneal longus, provides an abundant nerve supply. The combination of the muscle contraction and the topical pressure from the peroneal longus buttress 140 stimulates the superficial peroneal nerve and leads to a quick response through the nervous system and prevents a possible ankle injury. Thus, the increased neuromuscular communication caused by the peroneal longus buttress 140 works together with the proprioception mechanism to reduce the chance of injury. In other words, peroneal performance can be enhanced to protect lateral ligaments and reduce a risk of injury by isolating, activating, and training muscles to stimulate or shorten a stretch reflex, reduce or shorten latency in muscle spindles, and speed up a reaction time of muscles by reducing delay in muscle reaction times. Topical pressure delivered to peroneal longus buttress 140 can activate, engage, stimulate, "fire," or strengthen the peroneal longus and reduce pain, muscle fatigue, and discomfort of a patient or user. The length of the peroneal longus buttress 140 is preferably no more than about 5.08 cm or 2 inches long and more preferably between 3.81-5.08 cm or 1.5-2 inches long. The width of the peroneal longus buttress 140 is preferably no more than 2.54 cm or 1 inch wide. The peroneal longus buttress 140 is preferably no more than 0.84 cm or ⅓ inches thick, and more preferably, is about 0.64 cm or ¼ inches thick. In a preferred embodiment, the peroneal longus buttress 140 is substantially elliptical. The pressure applied by the peroneal longus buttress 140 is preferably between 5 and 30 mmHg, more preferably between 8 and 20 mmHg, and most preferably between 10 and 15 mmHg.

Preferably, the first malleolus bone buttress 145 is configured such that when topical leg gear 100 is worn by a user, the first malleolus bone buttress 145 applies sufficient pressure to the user's back side of the medial malleolus to increase neuromuscular communication, proprioception or both and reduce the chance of injury. Most preferably, the first malleolus bone buttress 145 touches the posterior aspect of the malleolus on the medial side. Preferably, the second malleolus bone buttress 150 is configured such that when topical leg gear 100 is worn by a user, the second malleolus bone buttress 150 applies sufficient pressure to the user's back side of the lateral malleolus to increase neuromuscular communication, proprioception or both and reduce the chance of injury. Most preferably, the second malleolus bone buttress 150 touches the posterior aspect of the malleolus on the lateral side. In their preferred embodiment, first and second malleolus bone buttresses 145 and 150 are substantially elliptical and are comprised of a compressible material. Flexible sleeve 110 compresses first and second malleolus bone buttresses 145 and 150 toward the user's medial and lateral malleolus with a force sufficient to stimulate sensory and tactile receptors in the foot and ankle. Preferably, the compressible material is suitable to conform to the back side and around the medial and lateral malleolus and apply pressure to one or more constituents of the peroneal muscle group. Most preferably, the first and second malleolus bone buttresses 145 and 150 stimulate the peroneal longus, peroneous brevis, and/or tibialis anterior muscle spindles. In other words, performance of peroneal longus, peroneous brevis, and/or tibialis anterior muscle spindles can be enhanced to protect lateral ligaments and reduce a risk of injury by isolating, activating, and training muscles to stimulate or shorten a stretch reflex, reduce or shorten latency in muscle spindles, and speed up a reaction time of muscles by reducing delay in muscle reaction times. Topical pressure delivered to first and second malleolus bone buttresses 145 and 150 can activate, engage, stimulate, "fire," or strengthen the peroneal longus, peroneous brevis, and/or tibialis anterior muscle spindles and reduce pain, muscle fatigue, and discomfort of a patient or user. Preferably, the first and second malleolus bone buttresses 145 and 150 are no more than about 0.84 cm or ⅓ inches thick, and more preferably, are about 0.64 cm or ¼ inches thick. In one specific preferred embodiment, the pressure applied by the first and second malleolus bone buttresses 145 and 150 is preferably between 5 and 40 mmHg, more preferably between 10 and 30 mmHg, and most preferably 20-25 mmHg.

The lateral foot-ankle buttress 155 is configured such that when topical leg gear 100 is worn by a user, the lateral foot-ankle buttress 155 applies sufficient pressure to the user's lateral ligaments of the ankle to increase proprioception and reduce the risk of injury. Although the lateral foot-ankle buttress primarily increases proprioception, it may also increase neuromuscular communication. The lateral ligaments of the user's ankle include the anterior talofibular, calcaneo fibular and posterior talofibular ligaments. For example, as the ankle is stressed into inversion and plantar flexion the ligaments begin to bow over the talus creating pressure from the lateral foot-ankle buttress 155, which sets off proprioception responses. The lateral foot-ankle buttress 155 will advantageously stimulate the sensory and tactile receptors of a user's foot and ankle when worn. Preferably, the taco-shaped lateral buttress 155, when properly positioned, places topical pressure on tactile receptors in the anterior talofibular ligament and calcaneo fibular ligaments. More preferably, the taco-shaped lateral foot-ankle buttress 155 will stimulate the stretch reflex, thereby reducing the latency period in the attached muscle spindles by at least one millisecond. After extended use (1-2 weeks) the taco-shaped lateral foot-ankle buttress 155 reduces the latency period by up to 50 milliseconds. Sustained use (4 or more weeks) of the taco-shaped lateral foot-ankle buttress 155 may reduce the latency period by at least 51 milliseconds. The combination of the peroneal longus buttress 140, the first and second malleolus bone buttresses 145 and 150, and the lateral foot-ankle buttress 155 may reduce the latency period by 100 to 250 milliseconds.

The lateral foot-ankle buttress has at least a first pair of openings 175 disposed between a flared upper portion 160 and a medial portion 165, wherein the first pair of openings 175 is divided by a first segment 180 of the lateral foot-ankle buttress 155. In one embodiment, the first pair of openings 175 is asymmetrical and comprises at least 10% of the total area of the lateral foot-ankle buttress 155. In other embodiments, the first pair of openings 175 comprises at least 40% of the total area of the lateral foot-ankle buttress 155. The lateral foot-ankle buttress 155, in some embodiments, may also have a second pair of openings 185 disposed between the medial portion 165 and a flared lower portion 170, wherein the second pair of openings 185 is divided by a second segment 190 of the lateral foot ankle buttress 155. In one embodiment, the second pair of openings 185 is asymmetrical and comprises at least 10% of the total area of lateral foot-ankle buttress 155. In an alternate embodiment, the second pair of openings 185 is symmetrical and comprises at least 10% of the total area of the lateral foot-ankle buttress 155. In yet another embodiment, the second pair of openings 185 comprises at least 40% of the total area of the lateral foot-ankle buttress 155.

Figure 7:
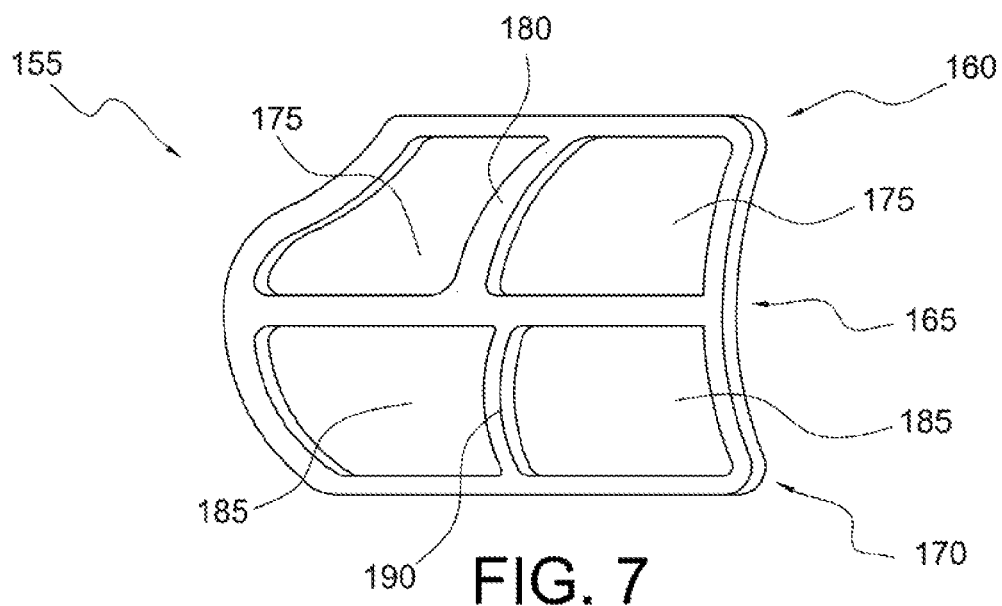
FIG. 7 is a side view of a lateral foot-ankle buttress with two pairs of openings used as topical leg gear.

In a preferred embodiment illustrated in FIG. 7, the lateral foot-ankle buttress 155 is comprised of the flared upper portion 160, the medial portion 165, and the flared lower portion 170 with the first pair of openings 175 and the second pair of openings 185 as described above. The flared upper portion 160 extends over and provides resistance to an anterior (top) portion of the foot of a user. Preferably, the flared upper portion 160 is further configured to fit under—and in close proximity to—a user's malleolus. The medial portion 165 of lateral foot-ankle buttress 155 is configured to conform to and extend around a user's foot, thereby providing resistance to a lateral portion of the foot. The flared lower portion 170 is also configured to extend around and provide resistance to a lower lateral portion of the foot. In alternate embodiments, the flared portion 170 may be configured to extend under and provide resistance to a posterior portion of the foot (the sole of the foot).

Figure 8:
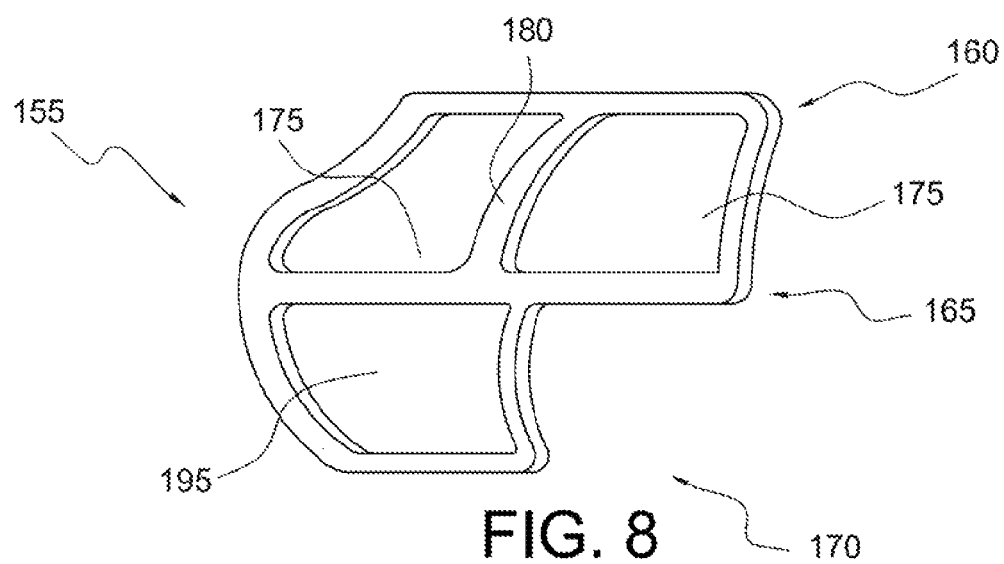
FIG. 8 is a side view of a lateral foot-ankle buttress with one pair of openings and one single opening used as topical leg gear.
Figure 9:
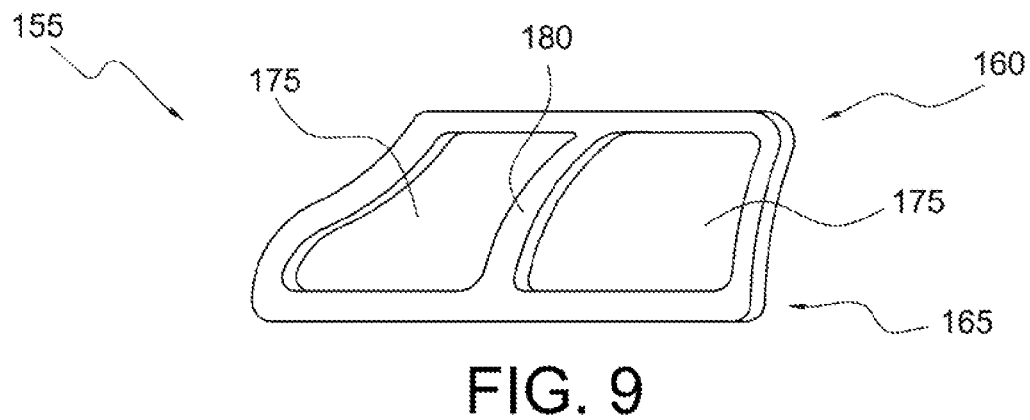
FIG. 9 is a side view of a lateral foot-ankle buttress with a single pair of openings used as topical leg gear.

In a more preferred embodiment, the lateral foot-ankle buttress 155 comprises the flared upper portion 160, the medial portion 165, and the flared lower portion 170 with the first pair of openings 175 and only one opening 195 between the medial portion 165 and the flared lower portion 170, as illustrated in FIG. 8. The location and function of the flared upper portion 160, the medial portion 165 and the flared lower portion 170 are the same in this embodiment as previously described. In a most preferred embodiment, the lateral foot-ankle buttress 155 comprises the flared upper portion 160 and the medial portion 165 with the first pair of openings 175. This embodiment does not include the flared lower portion 170 or the second pair of openings 185, as illustrated in FIG. 9. The location and function of the flared upper portion 160 and the medial portion 165 are the same in this embodiment as previously described. As this most preferred embodiment lacks the flared lower portion 170, the focus of the lateral foot-ankle buttress is to provide resistance to the anterior and lateral portion of the foot.

In a specific non-limiting preferred embodiment, the lateral foot-ankle buttress is typically about 0.32 cm or ⅛ inches thick and preferably applies between 5 and 35 mmHg of pressure, more preferably between 10 and 30 mmHg of pressure, and most preferably 15 and 25 mmHg of pressure.

In order to enhance an athlete's performance and reduce the chance of injury, topical leg gear 100 is applied to a user's leg during physical activity over an interval of time. Typically, the topical leg gear 100 is worn by a user during activities including resistance training, agility training, endurance training, rehabilitation and competitive activities, though it may be worn at other times to reduce the risk of injury.

In an alternate embodiment, topical leg gear 100 is included in a proprioceptive topical leg gear kit (not shown). Preferably, the kit includes, separately, a flexible sleeve 110 with an interior surface 115 and an exterior surface 120, and at least one buttress. More preferably, the kit includes a peroneal longus buttress 140, a first and second malleolus bone buttresses 145 and 150, and a lateral foot-ankle buttress 155, which when the kit is assembled and the leg gear 100 worn by a user, are positioned over the user's belly portion of the peroneal longus muscle, the back side of the user's medial and lateral malleolus and the user's lateral ligaments of the ankle, respectively. In this configuration, the buttresses 140, 145, 150 and 155 reduce the chance of injury and increase proprioception, neuromuscular communication or both to correct a user's talus to its normal anatomical relationship within a user's fibula-tibia joint. The flexible sleeve 110 and the buttresses 140, 145, 150 and 155 may be in the form of any embodiment discussed previously regarding topical leg gear 100.

In a preferred embodiment, the kit further comprises a shin guard 130. In a more preferred embodiment, the kit includes printed instructions relating to the use of topical leg gear 100, including instructions to couple the at least one buttress to the flexible sleeve 110.

Upon reading the teachings of this specification, those with ordinary skill in the art will appreciate that, under certain circumstances, considering issues such as changes in technology, user requirements, etc., a variety of fastening devices may be used to "affix", "couple", and/or "releasably couple" (as those words are used herein) one or more components of the present invention. These fastening devices may include one or more of the following: adhesives, bolts, buckles, clasps, latches, locks, screws, snaps, clamps, connectors, couplings, ties, or other fastening means yet to be developed.

The invention is therefore not to be limited to the particular embodiments described and illustrated herein. Although the foregoing describes the preferred embodiments of this invention, it will be understood that the broadest scope of this invention includes modifications. Such scope is limited only by the claims below as read in connection with the above specification. Moreover, many additional advantages of the present invention will be apparent to those skilled in the art in view of the above specification and claims herein.

What is claimed is:

1. Topical leg gear for enhancing performance and/or reducing the chance of injury, the leg gear comprising:
    a flexible sleeve; and a system of buttresses coupled to the flexible sleeve, the system comprising:
- a peroneal longus buttress positioned over a user's peroneal longus muscle belly when worn by a user and configured to apply sufficient pressure to increase proprioception, neuromuscular communication, or both in the user's peroneal longus muscle,
- two malleolus bone buttresses comprising a first malleolus bone buttress positioned on a back side of a user's medial malleolus when worn by a user and a second malleolus bone buttress positioned on a back side of a user's lateral malleolus when worn by the user, wherein the two malleolus bone buttresses are configured to apply sufficient pressure to increase proprioception, neuromuscular communication, or both in a user's ankle, and
- a lateral foot-ankle buttress positioned over a user's lateral ligaments of the ankle when worn by the user and configured to apply sufficient pressure to increase proprioception, neuromuscular communication, or both in the user's lateral ligaments of the ankle.

2. The topical leg gear of claim 1, wherein the flexible sleeve further comprises a sock sized to extend from a user's toe to about a user's knee.

3. The topical leg gear of claim 2, wherein the flexible sleeve further comprises a pocket coupled to the flexible sleeve and configured to receive a shin guard to protect a shinbone.

4. The topical leg gear of claim 1, wherein the peroneal longus buttress is no more than 5.08 centimeters (cm) long, 2.54 cm wide, and 0.84 cm thick.

5. The topical leg gear of claim 1, wherein the flexible sleeve is further configured such that the system of buttresses coupled to the flexible sleeve applies between 15-25 mmHg compression when worn by the user.

6. The topical leg gear of claim 1, wherein the peroneal longus buttress and the first and second malleolus bone buttresses are substantially elliptical.

7. The topical leg gear of claim 1, wherein the lateral foot-ankle buttress is no more than 0.32 centimeters thick.

8. Topical leg gear for enhancing performance and/or reducing the chance of injury, the leg gear comprising:
- a flexible sleeve; and
- a system of buttresses coupled to the flexible sleeve, the system comprising:
  - one or more malleolus bone buttresses positioned on a back side of a user's medial malleolus and on a back side of a user's lateral malleolus when worn by a user, and
  - a lateral foot-ankle buttress positioned over a user's lateral ligaments of an ankle when worn by the user.

9. The topical leg gear of claim 8, wherein the system of buttresses coupled to the flexible sleeve further comprises a peroneal longus buttress positioned over a user's peroneal longus muscle belly when worn by the user, the system of buttresses being configured to apply sufficient pressure to increase proprioception, neuromuscular communication, or both in the user's peroneal longus muscle, the user's ankle, and the user's lateral ligaments of the ankle to stimulate a stretch reflex and reduce a latency period in the user's peroneal longus muscle.

10. The topical leg gear of claim 9, wherein the peroneal longus buttress is no more than 5.08 centimeters (cm) long, 2.54 cm wide, and 0.84 cm thick.

11. The topical leg gear of claim 8, wherein the flexible sleeve is further configured such that the system of buttresses coupled to the flexible sleeve applies between 15-25 mmHg compression when worn by the user.

12. The topical leg gear of claim 8, wherein the flexible sleeve is further configured to receive a shin guard to protect a user's shinbone.

13. The topical leg gear of claim 8, wherein the lateral foot-ankle buttress comprises:
- a flared upper portion having a first region that is configured to extend over and provide resistance to an anterior portion of a user's foot and a second region that is configured to fit in close proximity to, but under a user's lateral malleolus; and
- a medial portion configured to conform to and extend around the user's foot, while providing resistance to a lateral portion of the user's foot.

14. The topical leg gear of claim 13, further comprising a flared lower portion configured to extend under and provide resistance to either a lower lateral portion or a posterior portion of the user's foot.

15. A system of topical pressure buttress placements to enhance performance and/or reduce the chance of injury, the system comprising:
- a primary buttress placement located on a portion of skin over a muscle portion of a user's peroneal longus;
- a secondary buttress placement located on a portion of skin on a back side of a user's medial malleolus and lateral malleolus;
- a tertiary buttress placement located on a portion of skin over a user's lateral ligaments of an ankle.

16. The system of topical pressure buttress placements of claim 15, comprising placing the primary buttress, secondary buttress, and tertiary buttress to a user's leg during physical activities over an interval of time.

17. The system of topical pressure buttress placements of claim 15, wherein the system of buttresses is configured to increase proprioception, neuromuscular communication, or both to correct a user's talus to its normal anatomical relationship within a user's fibula-tibia joint.

18. The system of topical pressure buttress placements of claim 15, wherein a flexible sleeve is configured such that the system of buttresses is coupled to the flexible sleeve and applies between 15-25 mmHg compression when worn by a user.

19. The system of topical pressure buttress placements of claim 15, further comprising a flexible sleeve comprising a material that provides 4-way compression.

20. The system of topical pressure buttress placements of claim 15, wherein a flexible sleeve is configured to receive a shin guard to protect a user's shinbone.

* * * * *